United States Patent
Buijink et al.

(10) Patent No.: US 7,294,727 B2
(45) Date of Patent: Nov. 13, 2007

(54) CATALYST PREPARATION

(75) Inventors: Jan Karel Frederik Buijink, Amsterdam (NL); Frank Joan Janssen, Zwaag (NL)

(73) Assignee: Shell Oil Company, Houston, TX (US)

( * ) Notice: Subject to any disclaimer, the term of this patent is extended or adjusted under 35 U.S.C. 154(b) by 693 days.

(21) Appl. No.: 10/720,921

(22) Filed: Nov. 24, 2003

(65) Prior Publication Data
US 2004/0158085 A1   Aug. 12, 2004

(30) Foreign Application Priority Data

Dec. 2, 2002  (EP) .................. 02258294
Dec. 2, 2002  (EP) .................. 02258296

(51) Int. Cl.
C07D 301/12  (2006.01)
C07D 301/19  (2006.01)
B01J 21/06   (2006.01)
B01J 21/08   (2006.01)

(52) U.S. Cl. ............ 549/529; 549/531; 502/239; 502/242

(58) Field of Classification Search ........... 549/529, 549/531; 502/239, 242
See application file for complete search history.

(56) References Cited

U.S. PATENT DOCUMENTS

| | | | |
|---|---|---|---|
| 3,829,392 A | 8/1974 | Wulff | 252/430 |
| 3,923,843 A | 12/1975 | Wulff | 260/348.5 |
| 5,932,751 A | 8/1999 | Carroll et al. | 549/529 |
| 6,011,162 A | 1/2000 | Han et al. | 549/529 |
| 6,114,552 A | 9/2000 | Han et al. | 549/529 |
| 6,383,966 B1 | 5/2002 | Han et al. | 502/63 |

FOREIGN PATENT DOCUMENTS

| | | |
|---|---|---|
| EP | 0170334 | 2/1986 |
| EP | 0438133 | 7/1991 |
| EP | 345856 | 8/1992 |
| EP | 0525503 | 2/1993 |
| EP | 734764 | 10/1996 |
| GB | 1525386 | 9/1978 |
| WO | WO9507305 | 3/1995 |
| WO | 98/50374 | 11/1998 |
| WO | WO0072961 | 12/2000 |
| WO | 02/48126 | 6/2002 |

OTHER PUBLICATIONS

International Search Report, dated Nov. 24, 2003.

*Primary Examiner*—Bernard Dentz

(57) ABSTRACT

The invention relates to a process for the preparation of an epoxidation catalyst which process involves (a) drying a silica gel carrier having a weight average particle size of from 0.1 mm to 2 mm at a temperature of from more than 200° C. to 300° C., and (b) contacting the carrier obtained in step (a) with a gas stream containing titanium halide to obtain an impregnated carrier, and the use of such catalyst in the preparation of alkylene oxide.

20 Claims, No Drawings

CATALYST PREPARATION

FIELD OF THE INVENTION

The present invention relates to the preparation of an epoxidation catalyst and to the process of preparing an alkylene oxide by using such catalyst.

BACKGROUND OF THE INVENTION

An epoxidation catalyst is understood to be a catalyst which catalyzes the production of an epoxy group containing compound. One process comprises contacting organic hydroperoxide and alkene with a heterogeneous epoxidation catalyst and withdrawing a product stream comprising alkylene oxide and an alcohol.

Catalysts for the manufacture of an epoxy group containing compound are known. EP-A-345856 describes the preparation of such a catalyst comprising impregnating a silicon compound with a stream of gaseous titanium tetrachloride preferably comprising an inert gas. In the example, it is mentioned that dried silica is used.

U.S. Pat. No. 6,114,552 teaches the use of a high surface area silica support or the like having a surface area greater than 1100 $m^2/g$ in preparing epoxidation catalysts. The high surface area solid is impregnated with either a solution of a titanium halide in a non-oxygenated hydrocarbon solvent or a gas stream of titanium tetrachloride. It is mentioned that it is desirable to dry the silica support prior to impregnation, for example by heating for several hours at a temperature of at least 200 to 700° C. The exemplified silica supports, to be impregnated with gaseous titanium tetrachloride, were dried at 450° C. in air.

U.S. Pat. No. 5,932,751 describes the preparation of titanium on silica catalysts in which the silica has been washed prior to the deposition of the titanium component thereon. A solution is used for depositing the titanium component.

There is a continuous interest in improving the selectivity of epoxidation catalysts in general, and more specifically of catalysts for the preparation of alkylene oxide.

SUMMARY OF THE INVENTION

The present invention provides a process for the preparation of an epoxidation catalyst which process comprises:

(a) drying a silica gel carrier, comprising silicon, having a weight average particle size of from 0.1 mm to 2 mm, at a temperature of from more than 200° C. to 300° C., and (b) contacting the carrier obtained in step (a) with a gas stream containing titanium halide to obtain an impregnated carrier.

DETAILED DESCRIPTION OF THE INVENTION

It has been found that the selectivity of an epoxidation catalyst is influenced by the way in which the silica gel carrier has been dried before impregnation. A more selective catalyst may be obtained if the water is removed from the silica carrier at a temperature in the range of from more than 200° C. to 300° C. before contact with the gaseous titanium chloride. Without wishing to be bound to any theory, it is thought that drying in this temperature range creates surface sites which have improved selectivity after having been reacted with gaseous titanium compounds.

An advantage of drying at relatively low temperature is a reduction in the time required for catalyst preparation. Additionally, an improved selectivity has been observed from having a low drying temperature.

The present invention provides a process for the preparation of an epoxidation catalyst which process comprises:

a) drying a silica gel carrier, comprising silicon, having a weight average particle size of from 0.1 mm to 2 mm, at a temperature of from more than 200° C. to 300° C., and b) contacting the carrier obtained in step (a) with a gas stream containing titanium halide to obtain an impregnated carrier.

A preferred preparation method comprises performing the drying of step (a) at a temperature which is higher than the temperature at which the impregnation of step (b) is performed. The impregnation temperature is the temperature of the silica carrier before being brought into contact with the gaseous titanium halide. When the silica carrier reacts with the titanium halide, the temperature of the carrier increases due to the exothermic nature of the reaction.

Drying the carrier ensures that there is no substantial amount of water present during impregnation of the silica gel carrier with titanium halide in order to avoid the reaction of titanium halide with water. This reaction forms compounds, such as titanium oxide, which do not contribute to the catalysis of the epoxidation reaction.

Contaminants may influence the performance of the final catalyst. It has been found that gas phase impregnation according to the present invention gives especially good results if the silica carrier contains at most 1200 ppm of sodium, more specifically at most 1000 ppm of sodium. Further, the silica carrier preferably comprises at most 500 ppm of aluminium, at most 500 ppm of calcium, at most 200 ppm of potassium, at most 100 ppm of magnesium and at most 100 ppm of iron.

The silica gel carrier for use in the present invention can in principle be any carrier derived from a silicon containing gel. In general, silica gels are a solid, amorphous form of hydrous silicon dioxide distinguished from other hydrous silicon dioxides by their microporosity and hydroxylated surface. Silica gels usually contain three-dimensional networks of aggregated silica particles of colloidal dimensions. They are typically prepared by acidifying an aqueous sodium silicate solution to a pH of less than 11 by combining it with a strong mineral acid. The acidification causes the formation of monosilicilic acid $(Si(OH)_4)$, which polymerizes into particles with internal siloxane linkages and external silanol groups. At a certain pH, the polymer particles aggregate, thereby forming chains and ultimately gel networks. Silicate concentration, temperature, pH and the addition of coagulants affect gelling time and final gel characteristics such as density, strength, hardness, surface area and pore volume. The resulting hydrogel is typically washed free of electrolytes, dried and activated. A suitable silica gel carrier would be silica support V432 and DAVICAT P-732, which are commercially available from Grace Davison.

The silica gel carrier for use in the present invention preferably has a surface area of at most 1000 $m^2$/gram, more preferably at most 800 $m^2$/gram, most preferably at most 500 $m^2$/gram. Generally, the surface area will be at least 10 $m^2$/gram, more specifically at least 20 $m^2$/gram. Silica gel carriers which were found especially suitable had a surface area of 300 $m^2$/g.

Silica gel carriers having a weight average particle size of substantially more than 2 mm, such as silica G 57 ex Grace, were found not to be suitable for use in the present invention. Particle sizes which were found to be especially suitable were weight average particle sizes of from 0.2 mm to 1.8 mm, more specifically of from 0.4 mm to 1.6 mm, most specifically of from 0.6 mm to 1.4 mm.

A further improvement was observed if the silicon containing carrier was subjected to a pretreatment comprising calcining the silicon containing carrier and subsequently hydrolyzing the carrier obtained. Hydrolysis comprises treating the carrier with water or steam. Preferably, the hydrolysis is carried out with steam. Alternatively, the hydrolysis treatment may comprise a washing treatment using an aqueous solution of a mineral acid, an aqueous solution of an ammonium salt or a combination thereof. Any water which might still be present after the hydrolysis is preferably removed before treating the carrier further. Water is preferably removed by drying. Preferably, the calcination is carried out at a relatively high temperature. The preferred high temperature calcination treatment comprises (a) calcining a silica gel carrier at a temperature of at least 400° C., (b) hydrolyzing the calcined silica gel carrier, (c) impregnating the hydrolyzed carrier obtained in step (b) with a titanium-containing impregnating agent, and (d) calcining the impregnated carrier. Preferably, the calcination of step (a) is carried out at a temperature of from 450° C. to 800° C., more preferably of from 500° C. to 700° C. If such high temperature calcination treatment is carried out, the drying according to the present invention is carried out on the calcined and hydrolyzed carrier.

Drying according to the present invention comprises subjecting the silicon containing carrier to a temperature of from more than 200° C. to 300° C. The time during which the drying is carried out, strongly depends on the kind of silica gel used and the pretreatment of the silica gel. However, the drying will generally be carried out for a period of time of from 15 minutes up to 10 hours, more specifially of from 1 hour to 8 hours, more specifically of from 1 hour to 5 hours. More specifically, the drying is carried out at a temperature of at least 210° C., preferably more than 210° C., more preferably at least 220° C., more preferably at least 225° C. The drying temperature is further preferably less than 300° C., more preferably at most 290° C., more preferably less than 290° C., more preferably at most 280° C., most preferably at most 275° C. Most preferably, the drying temperature is about 250° C.

It was found that a silica gel carrier which had been dried in this way had the type of surface which gave an excellent catalyst upon impregnation with gaseous titanium halide.

Furthermore, it has been found especially advantageous if the amount of titanium halide supplied in step (b) is such that the molar ratio of titanium to silicon of the carrier is in the range of from 0.050 to 0.063. It has been found that such molar ratio gives a more selective catalyst than similar catalysts of which the dried carrier had been in contact with either more titanium halide or less titanium halide. Without wishing to be bound to any theory, it is thought that this specific molar ratio gives a bonding of the titanium compounds which is especially advantageous for the selectivity of the catalyst.

Generally, the silicon containing carrier is contacted with the titanium halide in the course of from 0.1 hours and 10 hours, more specifically of from 0.5 hours to 6 hours. Preferably, at least 30% wt of the titanium is added during the first 50% of the impregnation time. The time of impregnation is taken to be the time during which the silicon containing carrier is in contact with gaseous titanium halide. Most preferably, the silicon containing carrier is contacted with a similar amount of titanium halide during the full time of the impregnation. However, it will be clear to someone skilled in the art that deviations from this are allowable such as at the start of the impregnation, at the end of the impregnation and for relatively short time intervals during impregnation.

Titanium halides which may be used comprise tri- and tetra-substituted titanium complexes which have from 1 to 4 halide substituents with the remainder of the substituents, if any, being alkoxide or amino groups. The titanium halide can be either a single titanium halide compound or can be a mixture of titanium halide compounds. Preferably, the titanium halide comprises at least 50% wt of titanium tetrachloride, more specifically at least 70% wt of titanium tetrachloride. Most preferably, the titanium halide is titanium tetrachloride.

The present invention comprises the use of a gas stream comprising titanium halide. Preferably, the gas stream consists of titanium halide optionally in combination with an inert gas. If an inert gas is present, the inert gas preferably is nitrogen. Especially selective catalysts were found to be obtainable through the use of a gas stream solely consisting of titanium halide. In such process, the preparation is carried out in the absence of a carrier gas. However, limited amounts of further gaseous compounds are allowed to be present during the contact between the silicon containing carrier and the gaseous titanium halide. The gas in contact with the carrier during impregnation preferably consists of at least 70% wt of titanium halide, more specifically at least 80% wt, more specifically at least 90% wt, most specifically at least 95% wt. Specific preferred processes have been described in the co-pending patent application claiming priority of European application 02258296.9, which is hereby incorporated by reference.

Gaseous titanium halide may be prepared in any way known to someone skilled in the art. A simple and easy way comprises heating a vessel containing titanium halide to such temperature that gaseous titanium halide is obtained. If inert gas is to be present, the inert gas can be led over the heated titanium halide. Generally, the impregnated carrier will be calcined and subsequently hydrolyzed and optionally silylated before being used as a catalyst. Therefore, the present invention further relates to a process further comprising (c) calcining the impregnated carrier obtained in step (a), (d) hydrolyzing the calcined impregnated carrier, and optionally (e) contacting the carrier obtained in step (d) with a silylating agent.

It is believed that calcination removes hydrogen halide, more specifically hydrogen chloride which is formed upon reaction of titanium halide and silicon compounds present on the surface of the silicon containing carrier.

The optional calcination of the impregnated carrier generally comprises subjecting the impregnated carrier to a temperature of at least 500° C., more specifically at least 600° C. Preferably, the calcination is carried out at a temperature of at least 650° C. From a practical point of view, it is preferred that the calcination temperature applied is at most 1000° C.

Hydrolysis of the impregnated and calcined carrier can remove titanium-halide bonds. The hydrolysis of the impregnated carrier generally will be somewhat more severe than the optional hydrolysis of the carrier before impregnation. Accordingly, the hydrolysis of the impregnated carrier is suitably carried out with steam at a temperature in the range of from 150° C. to 400° C.

Preferably, the hydrolyzed impregnated carrier is subsequently silylated. Silylation can be carried out by contacting the hydrolyzed impregnated carrier with a silylating agent, preferably at a temperature of between 100° C. and 425° C.

Suitable silylating agents include organosilanes like tetra-substituted silanes with $C_1$-$C_3$ hydrocarbyl substituents. A very suitable silylating agent is hexamethyldisilazane. Examples of suitable silylating methods and silylating agents are, for instance, described in U.S. Pat. No. 3,829,392 and U.S. Pat. No. 3,923,843 which are referred to in U.S. Pat. No. 6,011,162, and in EP-A-734764, all of which are hereby incorporated by reference.

The amount of titanium (as metallic titanium) will normally be in the range of from 0.1% to 10% by weight, suitably 1% to 5% by weight, based on total weight of the catalyst. Preferably, titanium or a titanium compound, such as a salt or an oxide, is the only metal and/or metal compound present.

As mentioned above, alkylene oxides, such as propylene oxide, may be produced by epoxidation of the corresponding olefin using a hydroperoxide such as hydrogen peroxide or an organic hydroperoxide as the source of oxygen. The hydroperoxide may be hydrogen peroxide or any organic hydroperoxide such as tert-butyl hydroperoxide, cumene hydroperoxide and ethylbenzene hydroperoxide. The alkene may be propene which results in propylene oxide as the alkylene oxide. The catalyst prepared according to the present invention has been found to give especially good results in such process. Therefore, the present invention further relates to a process for the preparation of alkylene oxide which process comprises contacting a hydroperoxide and alkene with a heterogeneous epoxidation catalyst and withdrawing a product stream comprising alkylene oxide and an alcohol and/or water, in which process the catalyst is according to the present invention.

A specific organic hydroperoxide is ethylbenzene hydroperoxide, in which case the alcohol obtained is 1-phenylethanol. The 1-phenylethanol usually is converted further by dehydration to obtain styrene.

Another method for producing propylene oxide is the co-production of propylene oxide and methyl tert-butyl ether (MTBE) starting from isobutane and propene. This involves similar reaction steps as the styrene/propylene oxide production process described in the previous paragraph. In the epoxidation step, tert-butyl hydroperoxide is reacted with propene, forming propylene oxide and tert-butanol. Tert-butanol is subsequently etherified into MTBE.

A further method comprises the manufacture of propylene oxide from cumene. In this process, cumene is reacted with oxygen or air to form cumene hydroperoxide. Cumene hydroperoxide thus obtained is reacted with propene in the presence of an epoxidation catalyst to yield propylene oxide and 2-phenyl propanol. The latter can be converted into cumene via a heterogeneous catalyst and hydrogen. Specific suitable processes are described for example in WO 02/48126, hereby incorporated by reference.

The conditions for the epoxidation reaction according to the present invention are those conventionally applied. For propene epoxidation reactions using ethylbenzene hydroperoxide, typical reaction conditions include temperatures of 50° C. to 140° C., suitably 75° C. to 125° C., and pressures up to 80 bar with the reaction medium being in the liquid phase.

The invention is further illustrated by the following Examples.

EXAMPLES 1 AND 2

The silica gel carrier used in the examples had a surface area of 300 $m^2$/g and a weight average particle size of about 1 mm. Substantially all particles had a particle size between 0.6 mm and 1.4 mm.

75 grams of this silica gel carrier was dried at different temperatures during 2 hours.

Subsequently, the dried silica gel carriers thus obtained were contacted with a gas stream consisting of titanium tetrachloride. The gas stream was obtained by heating titanium tetrachloride to 200° C. using an electrical heating system. The silica carrier was impregnated such as to obtain an impregnated carrier containing 3.63% wt of titanium of total amount of impregnated carrier.

The impregnated catalysts thus obtained were calcined at 600° C. during 7 hours. The calcined catalysts were subsequently contacted with steam at 325° C. for 6 hours. The steam flow consisted of 3 grams of water per hour and 8 Nl of nitrogen per hour. Finally, the catalysts were silylated at 185° C. for 2 hours by being contacted with 18 grams of hexamethyldisilazane per hour in a nitrogen flow of 1.4 Nl per hour.

The catalytic performance of the titanium catalyst samples was measured at 80° C. in a batch test unit consisting of a fixed bed reactor containing 15 grams of catalyst, a feed vessel containing 180 grams of feed and a circulation pump. A mixture of octene and 36% w ethylbenzene hydroperoxide in ethylbenzene was circulated through the catalyst bed at a constant rate of 5 kg/hr. The molar ratio of octene to ethylbenzene hydroperoxide was 2. The temperature of the feed vessel and catalytic bed was kept constant by means of circulating oil. The converted octene was replaced by helium on pressure control. After 2 hours, the reaction mixture was analyzed by on-line super critical fluid chromatography (SFC) to determine the selectivity of ethylbenzene hydroperoxide to octylene oxide.

In Table 1, the selectivities are given for the catalysts derived from carriers dried at different temperatures. The selectivity is the molar ratio of octylene oxide formed to ethylbenzene hydroperoxide converted.

TABLE 1

|  | Drying temperature (° C.) | Selectivity to octylene oxide (%) |
|---|---|---|
| Comparative catalyst A | 150 | 92.0 |
| Catalyst 1 | 225 | 92.2 |
| Catalyst 2 | 256 | 92.3 |
| Comparative catalyst B | 350 | 92.1 |

EXAMPLES 3 AND 4

Silica gel carriers as described in Examples 1 and 2 were dried at 250° C. during 2 hours.

Subsequently, the dried silica gel carriers thus obtained were contacted with a gas stream consisting of titanium tetrachloride. The gas stream was obtained by heating titanium tetrachloride to 200° C. using an electrical heating system. Table 2 describes the molar ratio of total amount of titanium tetrachloride led over the carrier to the amount of silicon present in the carrier. Further, the titanium loadings of the catalysts obtained are given in Table 2. The titanium loadings were determined by X-ray fluorescence methods. The catalysts have a similar titanium content while substantially different amounts of titanium chloride were used. Without wishing to be bound to any theory, it is thought that the similar titanium content is caused by the similar number of silanol groups available in the carriers.

The impregnated carriers were treated further as described in Examples 1 and 2.

The selectivity of the catalysts thus obtained was measured in an epoxidation process as described in Examples 1 and 2 with the exception that the feed contained propene instead of octene.

Table 2 gives analytical and performance data for the catalysts.

TABLE 2

|  | Ti (% w) | TiCl$_4$/Si ratio | Selectivity to propylene oxide (%) |
| --- | --- | --- | --- |
| Catalyst 3 | 3.63 | 0.061 | 77.2 |
| Catalyst 4 | 3.65 | 0.074 | 72.1 |

It will be clear from Table 2 that a catalyst having a titanium to silicon molar ratio of 0.061 gives a catalyst having a higher selectivity than a catalyst having a titanium to silicon molar ratio of 0.074. This is very surprising in view of the larger amount of titanium tetrachloride used in the preparation of the latter.

What is claimed is:

1. A process for the preparation of an epoxidation catalyst which process comprises:
    (a) drying a silica gel carrier, comprising silicon, having a weight average particle size of from 0.1 mm to 2 mm, at a temperature of from more than 200° C. to 300° C.; and,
    (b) contacting the carrier obtained in step (a) with a gas stream comprising titanium halide to obtain an impregnated carrier, wherein said sillica gel carrier has a surface area of at most 1,000 m$^2$/g.

2. The process of claim 1, wherein the drying of step (a) is performed at a temperature which is higher than the temperature at which the impregnation of step (b) is performed.

3. The process of claim 1, wherein the amount of titanium halide supplied in step (b) is such that the molar ratio of titanium halide added to silicon present in the carrier is from 0.050 to 0.063.

4. The process of claim 1, wherein the gas stream consists of titanium halide.

5. The process of claim 1, in which process the silica gel carrier has a surface area of at most 500 m$^2$/g.

6. The process of claim 1, wherein the silica gel carrier is dried for a period of time of from 1 hour to 8 hours.

7. The process of claim 1, further comprising:
    (c) calcining the impregnated carrier to obtain a calcined impregnated carrier; and,
    (d) hydrolyzing the calcined impregnated carrier.

8. The process of claim 7 further comprising:
    (e) contacting the carrier obtained in step (d) with a silylating agent.

9. The process of claim 8, wherein the drying of step (a) is performed at a temperature which is higher than the temperature at which the impregnation of step (b) is performed.

10. The process of claim 8, wherein the amount of titanium halide supplied in step (b) is such that the molar ratio of titanium halide added to silicon present in the carrier is from 0.050 to 0.063.

11. The process of claim 8, wherein the gas stream consists of titanium halide.

12. The process of claim 8, wherein the silica gel carrier has a surface area of at most 500 m$^2$/g.

13. The process of claim 8, wherein the silica gel carrier is dried for a period of time of from 1 hour to 8 hours.

14. The process of claim 8, wherein the calcining of step (c) is performed at a temperature of at least 500° C.

15. The process of claim 8, wherein the hydrolyzing of step (d) is performed at a temperature in the range of from 150° C. to 400° C.

16. The process of claim 8, wherein the silylating agent comprises hexamethyldisilazane.

17. A process for the preparation of an alkylene oxide which process comprises:
    contacting a hydroperoxide and an alkene with a heterogeneous epoxidation catalyst; and,
    withdrawing a product stream comprising an alkylene oxide and an alcohol and/or water, wherein the catalyst was prepared according to a process comprising:
    (a) drying a silica gel carrier, comprising silicon, having a weight average particle size of from 0.1 mm to 2 mm, at a temperature of from more than 200° C. to 300° C.; and,
    (b) contacting the carrier obtained in step (a) with a gas stream comprising titanium halide to obtain an impregnated carrier, wherin said sillica gel carrier has a surface area of at most 1,000 m$^2$/g.

18. The process of claim 8, wherein the alkene comprises propene and the alkylene oxide comprises propylene oxide.

19. The process of claim 8, wherein the hydroperoxide comprises ethylbenzene hydrogen peroxide and in which the alcohol comprises 1-phenyl ethanol.

20. The process of claim 10, further comprising dehydrating 1-phenylethanol to obtain styrene.

* * * * *